(12) United States Patent  (10) Patent No.: US 8,666,512 B2
Walker et al.  (45) Date of Patent: Mar. 4, 2014

(54) IMPLANTABLE MEDICAL DEVICE LEAD INCLUDING INNER COIL REVERSE-WOUND RELATIVE TO SHOCKING COIL

(75) Inventors: Joseph Walker, Shoreview, MN (US); David R. Wulfman, Minneapolis, MN (US); Devon N. Arnholt, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/620,934

(22) Filed: Sep. 15, 2012

(65) Prior Publication Data

US 2013/0116764 A1  May 9, 2013

Related U.S. Application Data (60) Provisional application No. 61/555,701, filed on Nov. 4, 2011.

(51) Int. Cl.
*A61N 1/39* (2006.01)

(52) U.S. Cl.
USPC ........................................................ 607/119

(58) Field of Classification Search
USPC ........................................................ 607/119
See application file for complete search history.

(56) References Cited

U.S. PATENT DOCUMENTS

| | | |
|---|---|---|
| 3,614,692 A | 10/1971 | Rozelle et al. |
| 4,131,759 A | 12/1978 | Felkel |
| 4,135,518 A | 1/1979 | Dutcher |
| 4,404,125 A | 9/1983 | Abolins et al. |
| 4,484,586 A | 11/1984 | McMickle et al. |
| 4,493,329 A | 1/1985 | Crawford et al. |
| 4,643,203 A | 2/1987 | Labbe |
| 4,869,970 A | 9/1989 | Gulla et al. |
| 5,056,516 A | 10/1991 | Spehr |

(Continued)

FOREIGN PATENT DOCUMENTS

| | | |
|---|---|---|
| CN | 1762510 A | 4/2006 |
| CN | 101039619 A | 9/2007 |

(Continued)

OTHER PUBLICATIONS

Gray, Robert W. et al., "Simple design changes to wires to substantially reduce MRI-induced heating at 1.5 T: implications for implanted leads", Magnetic Resonance Imaging 23 (2005) 887-891.

(Continued)

*Primary Examiner* — George Manuel
(74) *Attorney, Agent, or Firm* — Faegre Baker Daniels LLP (57) ABSTRACT

A medical device lead includes a proximal connector configured to couple the lead to a pulse generator and an insulative lead body extending distally from the proximal connector. The lead also includes an inner conductor and one or more cable conductors coupled to the proximal connector at a proximal end and extending through the lead body. The lead further includes one or more defibrillation coil electrodes coupled to a distal end of the one or more cable conductors. The one or more defibrillation coil electrodes are disposed around and electrically isolated from the inner conductor. The one or more defibrillation coil electrodes have a first winding direction and the inner conductor has a second winding direction opposite the first winding direction.

20 Claims, 4 Drawing Sheets

(56) References Cited

U.S. PATENT DOCUMENTS

| | | |
|---|---|---|
| 5,217,010 A | 6/1993 | Tsitlik et al. |
| 5,222,506 A | 6/1993 | Patrick et al. |
| 5,231,996 A | 8/1993 | Bardy et al. |
| 5,241,957 A | 9/1993 | Camp et al. |
| 5,243,911 A | 9/1993 | Dow et al. |
| 5,246,014 A | 9/1993 | Williams et al. |
| 5,330,522 A | 7/1994 | Kreyenhagen |
| 5,354,327 A | 10/1994 | Smits |
| 5,378,234 A | 1/1995 | Hammerslag et al. |
| 5,387,199 A | 2/1995 | Siman et al. |
| 5,425,755 A | 6/1995 | Doan |
| 5,456,707 A | 10/1995 | Giele |
| 5,483,022 A | 1/1996 | Mar |
| 5,522,872 A | 6/1996 | Hoff |
| 5,522,875 A | 6/1996 | Gates et al. |
| 5,554,139 A | 9/1996 | Okajima |
| 5,574,249 A | 11/1996 | Lindsay |
| 5,584,873 A | 12/1996 | Shoberg et al. |
| 5,599,576 A | 2/1997 | Opolski |
| 5,609,622 A | 3/1997 | Soukup et al. |
| 5,618,208 A | 4/1997 | Crouse et al. |
| 5,728,149 A | 3/1998 | Laske et al. |
| 5,760,341 A | 6/1998 | Laske et al. |
| 5,800,496 A | 9/1998 | Swoyer et al. |
| 5,810,887 A | 9/1998 | Accorti, Jr. et al. |
| 5,833,715 A | 11/1998 | Vachon et al. |
| 5,935,159 A | 8/1999 | Cross, Jr. et al. |
| 5,957,966 A | 9/1999 | Schroeppel et al. |
| 5,957,970 A | 9/1999 | Shoberg et al. |
| 5,968,087 A | 10/1999 | Hess et al. |
| 6,057,031 A | 5/2000 | Breme et al. |
| 6,078,840 A | 6/2000 | Stokes |
| 6,083,216 A | 7/2000 | Fischer, Sr. |
| 6,106,522 A | 8/2000 | Fleischman et al. |
| 6,141,593 A | 10/2000 | Patag |
| 6,143,013 A | 11/2000 | Samson et al. |
| 6,178,355 B1 | 1/2001 | Williams et al. |
| 6,208,881 B1 | 3/2001 | Champeau |
| 6,249,708 B1 | 6/2001 | Nelson et al. |
| 6,256,541 B1 | 7/2001 | Heil et al. |
| 6,259,954 B1 | 7/2001 | Conger et al. |
| 6,289,250 B1 | 9/2001 | Tsuboi et al. |
| 6,295,476 B1 | 9/2001 | Schaenzer |
| 6,400,992 B1 | 6/2002 | Borgersen et al. |
| 6,434,430 B2 | 8/2002 | Borgersen et al. |
| 6,456,888 B1 | 9/2002 | Skinner et al. |
| 6,493,591 B1 | 12/2002 | Stokes |
| 6,501,991 B1 | 12/2002 | Honeck et al. |
| 6,501,994 B1 | 12/2002 | Janke et al. |
| 6,510,345 B1 | 1/2003 | Van Bentem |
| 6,516,230 B2 | 2/2003 | Williams et al. |
| 6,526,321 B1 | 2/2003 | Spehr |
| 6,564,107 B1 | 5/2003 | Bodner et al. |
| 6,671,554 B2 | 12/2003 | Gibson et al. |
| 6,721,604 B1 | 4/2004 | Robinson et al. |
| 6,813,251 B1 | 11/2004 | Garney et al. |
| 6,850,803 B1 | 2/2005 | Jimenez et al. |
| 6,854,994 B2 | 2/2005 | Stein et al. |
| 6,920,361 B2 | 7/2005 | Williams |
| 6,925,334 B1 | 8/2005 | Salys |
| 6,949,929 B2 | 9/2005 | Gray et al. |
| 6,978,185 B2 | 12/2005 | Osypka |
| 6,993,373 B2 | 1/2006 | Vrijheid et al. |
| 6,999,821 B2 * | 2/2006 | Jenney et al. .................. 607/122 |
| 7,013,180 B2 | 3/2006 | Dublin et al. |
| 7,013,182 B1 | 3/2006 | Krishnan |
| 7,123,013 B2 | 10/2006 | Gray |
| 7,138,582 B2 | 11/2006 | Lessar et al. |
| 7,158,837 B2 | 1/2007 | Osypka et al. |
| 7,174,219 B2 | 2/2007 | Wahlstrand et al. |
| 7,174,220 B1 | 2/2007 | Chitre et al. |
| 7,205,768 B2 | 4/2007 | Schulz et al. |
| 7,257,449 B2 | 8/2007 | Bodner |
| 7,363,090 B2 | 4/2008 | Halperin et al. |
| 7,378,931 B2 | 5/2008 | Odahara et al. |
| 7,388,378 B2 | 6/2008 | Gray et al. |
| 7,389,148 B1 | 6/2008 | Morgan |
| 7,453,344 B2 | 11/2008 | Maeda et al. |
| 7,571,010 B2 | 8/2009 | Zarembo et al. |
| 7,610,101 B2 | 10/2009 | Wedan et al. |
| 7,765,005 B2 | 7/2010 | Stevenson |
| 7,917,213 B2 | 3/2011 | Bulkes et al. |
| 7,986,999 B2 | 7/2011 | Wedan et al. |
| 8,103,360 B2 | 1/2012 | Foster |
| 8,170,688 B2 | 5/2012 | Wedan et al. |
| 8,244,346 B2 | 8/2012 | Foster et al. |
| 8,332,050 B2 | 12/2012 | Perrey et al. |
| 8,335,572 B2 | 12/2012 | Ameri |
| 8,391,994 B2 | 3/2013 | Foster et al. |
| 8,401,671 B2 | 3/2013 | Wedan et al. |
| 2002/0065544 A1 | 5/2002 | Smits |
| 2002/0072769 A1 | 6/2002 | Silvian et al. |
| 2002/0111664 A1 | 8/2002 | Bartig et al. |
| 2002/0128689 A1 | 9/2002 | Connelly et al. |
| 2002/0144720 A1 | 10/2002 | Zahorik et al. |
| 2003/0050680 A1 | 3/2003 | Gibson et al. |
| 2003/0063946 A1 | 4/2003 | Williams et al. |
| 2003/0083723 A1 | 5/2003 | Wilkinson et al. |
| 2003/0083726 A1 | 5/2003 | Zeijlemaker et al. |
| 2003/0092303 A1 | 5/2003 | Osypka |
| 2003/0093138 A1 | 5/2003 | Osypka et al. |
| 2003/0139794 A1 | 7/2003 | Jenney et al. |
| 2003/0140931 A1 | 7/2003 | Zeijlemaker et al. |
| 2003/0144705 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0014355 A1 | 1/2004 | Osypka et al. |
| 2004/0064173 A1 | 4/2004 | Hine et al. |
| 2004/0064174 A1 | 4/2004 | Belden |
| 2004/0088033 A1 | 5/2004 | Smits et al. |
| 2004/0122490 A1 | 6/2004 | Reinke et al. |
| 2004/0162600 A1 | 8/2004 | Williams |
| 2004/0193140 A1 | 9/2004 | Griffin et al. |
| 2004/0243210 A1 | 12/2004 | Morgan et al. |
| 2004/0267107 A1 | 12/2004 | Lessar et al. |
| 2005/0030322 A1 | 2/2005 | Gardos |
| 2005/0070972 A1 | 3/2005 | Wahlstrand et al. |
| 2005/0090886 A1 | 4/2005 | MacDonald et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0182471 A1 | 8/2005 | Wang |
| 2005/0222642 A1 | 10/2005 | Przybyszewski et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0246007 A1 | 11/2005 | Sommer et al. |
| 2005/0272280 A1 | 12/2005 | Osypka |
| 2005/0283167 A1 | 12/2005 | Gray |
| 2006/0009819 A1 | 1/2006 | Przybyszewski |
| 2006/0030774 A1 | 2/2006 | Gray et al. |
| 2006/0041294 A1 | 2/2006 | Gray |
| 2006/0089691 A1 | 4/2006 | Kaplan et al. |
| 2006/0089695 A1 | 4/2006 | Bolea et al. |
| 2006/0089696 A1 | 4/2006 | Olsen et al. |
| 2006/0093685 A1 | 5/2006 | Mower et al. |
| 2006/0105066 A1 | 5/2006 | Teague et al. |
| 2006/0106442 A1 | 5/2006 | Richardson et al. |
| 2006/0167536 A1 | 7/2006 | Nygren et al. |
| 2006/0200218 A1 | 9/2006 | Wahlstrand |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2006/0293737 A1 | 12/2006 | Krishnan |
| 2007/0106332 A1 | 5/2007 | Denker et al. |
| 2007/0112398 A1 | 5/2007 | Stevenson et al. |
| 2007/0156205 A1 | 7/2007 | Larson et al. |
| 2007/0179577 A1 | 8/2007 | Marshall et al. |

(56) References Cited

U.S. PATENT DOCUMENTS

| | | |
|---|---|---|
| 2007/0179582 A1 | 8/2007 | Marshall et al. |
| 2007/0191914 A1 | 8/2007 | Stessman |
| 2007/0208383 A1 | 9/2007 | Williams |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0058902 A1 | 3/2008 | Gray et al. |
| 2008/0125754 A1 | 5/2008 | Beer et al. |
| 2008/0129435 A1 | 6/2008 | Gray |
| 2008/0132986 A1 | 6/2008 | Gray et al. |
| 2008/0243218 A1 | 10/2008 | Bottomley et al. |
| 2008/0262584 A1 | 10/2008 | Bottomley et al. |
| 2009/0099440 A1 | 4/2009 | Viohl |
| 2009/0099555 A1 | 4/2009 | Viohl et al. |
| 2009/0118610 A1 | 5/2009 | Karmarkar et al. |
| 2009/0149920 A1 | 6/2009 | Li et al. |
| 2009/0149933 A1 | 6/2009 | Ameri |
| 2009/0198314 A1 | 8/2009 | Foster et al. |
| 2009/0270956 A1 | 10/2009 | Vase et al. |
| 2009/0281608 A1 | 11/2009 | Foster |
| 2010/0010602 A1 | 1/2010 | Wedan et al. |
| 2010/0114277 A1 | 5/2010 | Zhao et al. |
| 2010/0174348 A1 | 7/2010 | Bulkes et al. |
| 2010/0234929 A1 | 9/2010 | Scheuermann |
| 2010/0331936 A1 | 12/2010 | Perrey et al. |
| 2011/0079423 A1 | 4/2011 | Zhao et al. |
| 2011/0087299 A1 | 4/2011 | Ameri |
| 2011/0093054 A1 | 4/2011 | Ameri |
| 2011/0160817 A1 | 6/2011 | Foster et al. |
| 2011/0160818 A1 | 6/2011 | Struve |
| 2011/0160828 A1 | 6/2011 | Foster et al. |
| 2011/0160829 A1 | 6/2011 | Foster et al. |
| 2011/0208280 A1 | 8/2011 | Li et al. |
| 2011/0218422 A1 | 9/2011 | Atalar et al. |
| 2011/0238146 A1 | 9/2011 | Wedan et al. |
| 2011/0288403 A1 | 11/2011 | Kondabatni et al. |
| 2012/0016451 A1 | 1/2012 | Struve et al. |
| 2012/0022356 A1 | 1/2012 | Olsen et al. |
| 2012/0035698 A1 | 2/2012 | Johnson et al. |
| 2012/0053662 A1 | 3/2012 | Foster et al. |
| 2012/0109270 A1 | 5/2012 | Foster |
| 2012/0161901 A1 | 6/2012 | Stevenson et al. |
| 2012/0179233 A1 | 7/2012 | Wedan et al. |
| 2012/0253340 A1 | 10/2012 | Stevenson et al. |
| 2012/0271394 A1 | 10/2012 | Foster et al. |
| 2013/0158641 A1 | 6/2013 | Foster et al. |
| 2013/0190849 A1 | 7/2013 | Perrey et al. |
| 2013/0190850 A1 | 7/2013 | Wedan et al. |

FOREIGN PATENT DOCUMENTS

| | | |
|---|---|---|
| EP | 0897997 B1 | 2/2003 |
| EP | 1594564 A1 | 11/2005 |
| JP | 2004141679 A | 5/2004 |
| JP | 2005501673 A | 1/2005 |
| JP | 2005515852 A | 6/2005 |
| JP | 2005515854 A | 6/2005 |
| WO | WO9606655 A1 | 3/1996 |
| WO | WO03089045 A2 | 10/2003 |
| WO | WO2004073791 A1 | 9/2004 |
| WO | WO2006105066 A2 | 3/2006 |
| WO | WO2006093685 A1 | 9/2006 |
| WO | WO2007047966 A2 | 4/2007 |
| WO | WO2007089986 A1 | 8/2007 |
| WO | WO2007118194 A2 | 10/2007 |
| WO | WO2009137186 A1 | 11/2009 |
| WO | WO2010078552 A1 | 7/2010 |

OTHER PUBLICATIONS

International Search Report and Written Opinion issued in PCT/US2008/085518 on Oct. 29, 2009, 15 pages.
International Search Report and Written Opinion issued in PCT/US2009/032838, mailed May 4, 2009, 14 pages.
International Search Report and Written Opinion issued in PCT/US2009/038629, mailed Jun. 29, 2009, 11 pages.
International Search Report and Written Opinion issued in PCT/US2010/024062, mailed Sep. 27, 2010.
International Search Report and Written Opinion issued in PCT/US2010/033686 on Aug. 10, 2010, 12 pages.
International Search Report and Written Opinion issued in PCT/US2010/055130, mailed Mar. 10, 2011, 11 pages.
International Search Report and Written Opinion issued in PCT/US2010/055653, mailed Feb. 1, 2011, 14 pages.
International Search Report and Written Opinion issued in PCT/US2012/055673, mailed Dec. 13, 2012, 10 pages.
Invitation to Pay Additional Fees and Partial Search Report, dated Aug. 17, 2009, issued in PCT/US2008/085533, 6 pages.
Invitation to Pay Additional Fees and Partial Search Report, issued in PCT/US2010/024062, mailed May 7, 2010.
Partial International Search Report issued in PCT/US2013/013432, mailed Jul. 17, 2013, 6 pages.

* cited by examiner

IMPLANTABLE MEDICAL DEVICE LEAD INCLUDING INNER COIL REVERSE-WOUND RELATIVE TO SHOCKING COIL

CROSS-REFERENCE TO RELATED APPLICATION

This application claims priority to Provisional Patent Application No. 61/555,701, filed Nov. 4, 2011, which is herein incorporated by reference in its entirety.

TECHNICAL FIELD

The present disclosure relates to implantable medical devices. More particularly, the present disclosure relates to a medical device lead including an inner coil conductor reverse-wound relative to one or more shocking coils.

BACKGROUND

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3 Teslas (T). During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage on the lead.

SUMMARY

Disclosed herein are various embodiments of a medical device lead including an inner conductive coil having a first winding direction and a defibrillation coil electrode having a second winding direction opposite the first winding direction, as well as medical device systems including such a lead.

In Example 1, a medical device lead includes a proximal connector configured to couple the lead to a pulse generator and an insulative lead body extending distally from the proximal connector. The lead also includes an inner conductor and one or more cable conductors coupled to the proximal connector at a proximal end and extending through the lead body. The lead further includes one or more defibrillation coil electrodes each coupled to a distal end of one of the one or more cable conductors. The one or more defibrillation coil electrodes are each disposed around and electrically isolated from the inner conductive coil. The one or more defibrillation coil electrodes each have a first winding direction and the inner conductive coil has a second winding direction opposite the first winding direction.

In Example 2, the medical device lead according to Example 1, wherein one or more defibrillation coils are separated from the inner conductor by an insulative layer.

In Example 3, the medical device lead according to either Example 1 or 2, wherein the inner conductor is coupled to one or more pace/sense electrodes at a distal end of the inner conductor.

In Example 4, the medical device lead according to any of Examples 1-3, wherein the inner conductor comprises one or more coils.

In Example 5, the medical device lead according to any of Examples 1-4, wherein at least one of the one or more coils is unifilar.

In Example 6, a medical device lead includes a first distal electrode, a first inner conductive coil having a distal end electrically coupled to the first distal electrode, a cable conductor, and a defibrillation coil electrode coupled to a distal end of the one or more cable conductors. The defibrillation coil is disposed around and electrically isolated from the first inner conductive coil. The defibrillation coil has a first winding direction and the first inner conductive coil has a second winding direction opposite the first winding direction.

In Example 7, the medical device lead according to Example 6, wherein one or more defibrillation coils are separated from the first inner conductive coil by an insulative layer.

In Example 8, the medical device lead according to either Example 6 or 7, wherein the first inner conductive coil is unifilar.

In Example 9, the medical device lead according to any of Examples 6-8, wherein the first distal electrode is a tip electrode.

In Example 10, the medical device lead according to any of Examples 6-9, wherein a temperature increase at the first electrode in an MRI environment is less than about 3.0° C.

In Example 11, the medical device lead according to any of Examples 6-10, and further comprising a second distal electrode and a second inner conductive coil having a distal end electrically coupled to the second distal electrode, wherein the second inner conductive coil has the second winding direction.

In Example 12, the medical device lead according to any of Examples 6-11, wherein the second inner conductive coil is unifilar.

In Example 13, the medical device lead according to any of Examples 6-12, wherein the second distal electrode is a ring electrode.

In Example 14, a medical device includes a pulse generator and a lead. The lead includes a proximal connector configured to couple the lead to the pulse generator, an insulative lead body extending distally from the proximal connector, and an inner conductive coil assembly and one or more cable conductors coupled to the proximal connector and extending through the lead body. The lead also includes one or more defibrillation coil electrodes each coupled to a distal end of one of the one or more cable conductors. The one or more defibrillation coil electrodes are disposed around and electrically isolated from the inner conductive coil. The one or more defibrillation coil electrodes have a first winding direction and the inner conductive coil has a second winding direction opposite the first winding direction.

In Example 15, the medical device according to Example 14, wherein the one or more defibrillation coils are separated from the inner conductive coil assembly by an insulative layer.

In Example 16, the medical device according to either Example 14 or 15, wherein the inner conductive coil assembly is coupled to one or more pace/sense electrodes at a distal end of the inner conductive coil assembly.

In Example 17, the medical device according to any of Examples 14-16, wherein the one or more pace/sense electrodes comprise at least one of a tip electrode and a ring electrode.

In Example 18, the medical device according to any of Examples 14-17, wherein a temperature increase at each of the one or more pace/sense electrodes in an MRI environment is less than about 3.0° C.

In Example 19, the medical device according to any of Examples 14-18, wherein the inner conductive coil assembly comprises one or more coils.

In Example 20, the medical device according to any of Examples 14-19, wherein at least one of the one or more coils is unifilar.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

Figure 1:
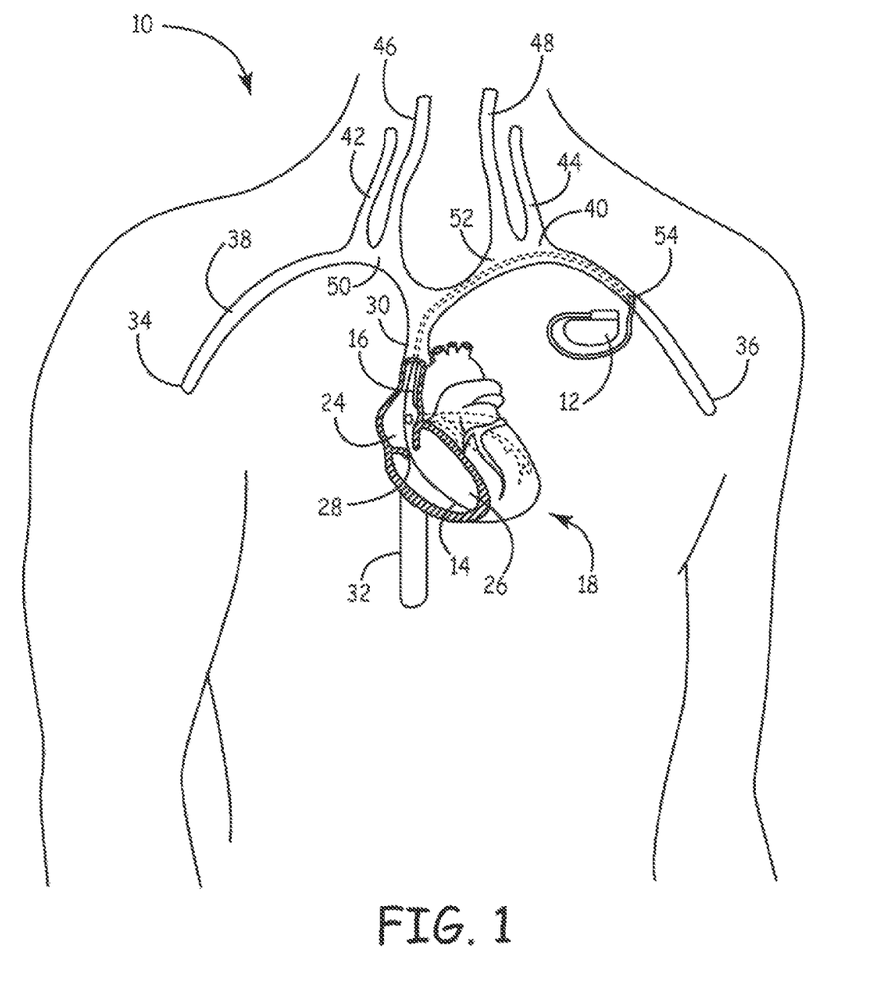
FIG. 1 is a schematic view of a cardiac rhythm management (CRM) system including a pulse generator and a lead implanted in a patient's heart according to an embodiment of the present disclosure.

FIG. 1 is a schematic view of a cardiac rhythm management (CRM) system 10 according to an embodiment of the present disclosure. As shown in FIG. 1, the CRM system 10 includes a pulse generator 12 coupled to a plurality of leads 14, 16 deployed in a patient's heart 18. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. The major veins supplying blood to the superior vena cava 30 include the right and left axillary veins 34 and 36, which flow into the right and left subclavian veins 38 and 40. The right and left external jugular 42 and 44, along with the right and left internal jugular 46 and 48, join the right and left subclavian veins 38 and 40 to form the right and left brachiocephalic veins 50 and 52, which in turn combine to flow into the superior vena cava 30.

The leads 14, 16 operate to convey electrical signals and stimuli between the pulse generator 12 and the heart 18. In the illustrated embodiment, the lead 14 is implanted in the right ventricle 26, and the lead 16 is implanted in the right atrium 24. In other embodiments, the CRM system 10 may include additional leads, e.g., a lead extending into a coronary vein for stimulating the left ventricle in a bi-ventricular pacing or cardiac resynchronization therapy system. As shown, the leads 14, 16 enter the vascular system through a vascular entry site 54 formed in the wall of the left subclavian vein 40, extend through the left brachiocephalic vein 52 and the superior vena cava 30, and are implanted in the right ventricle 26 and right atrium 24, respectively. In other embodiments, the leads 14, 16 may enter the vascular system through the right subclavian vein 38, the left axillary vein 36, the left external jugular 44, the left internal jugular 48, or the left brachiocephalic vein 52.

The pulse generator 12 is typically implanted subcutaneously within an implantation location or pocket in the patient's chest or abdomen. The pulse generator 12 may be an implantable medical device known in the art or later developed, for delivering an electrical therapeutic stimulus to the patient. In various embodiments, the pulse generator 12 is a pacemaker, an implantable cardiac defibrillator, and/or includes both stimulation and defibrillation capabilities. The portion of the leads 14, 16 extending from the pulse generator 12 to the vascular entry site 54 are also located subcutaneously or submuscularly. The leads 14, 16 are each connected to the pulse generator 12 via proximal connectors. Any excess lead length, i.e., length beyond that needed to reach from the pulse generator 12 location to the desired endocardial or epicardial implantation site, is generally coiled up in the subcutaneous pocket near the pulse generator 12.

The electrical signals and stimuli conveyed by the pulse generator 12 are carried to electrodes at the distal ends of leads 14, 16 by one or more conductors extending through the leads 14, 16. The one or more conductors are each electrically coupled to a connector suitable for interfacing with the pulse generator 12 at the proximal end of the leads 14, 16 and to one or more electrodes at the distal end.

Figure 2A:
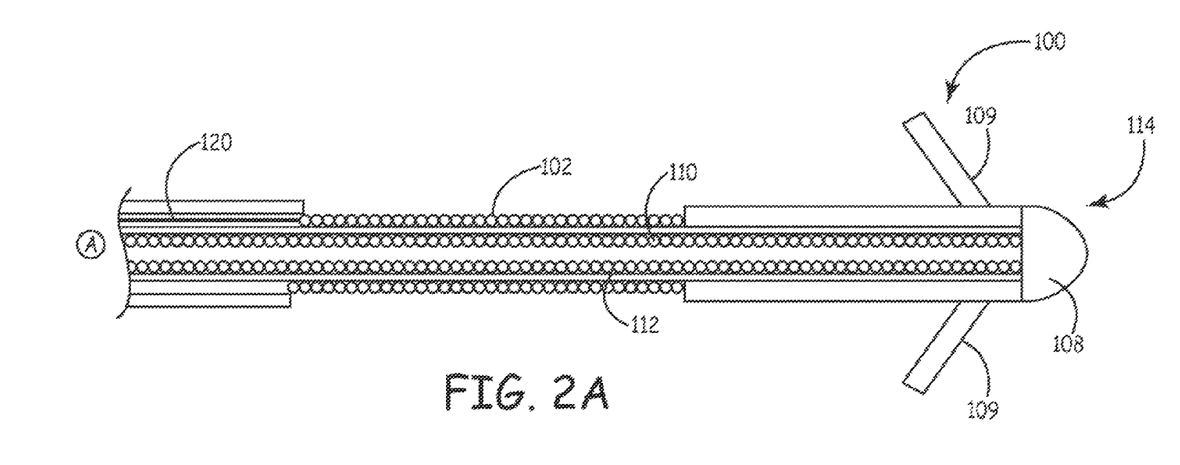
FIG. 2A is a schematic view of a distal portion of a lead according to an embodiment of the present disclosure including two defibrillation coils that are reverse-wound with respect to an inner conductive coil.
Figure 2B:
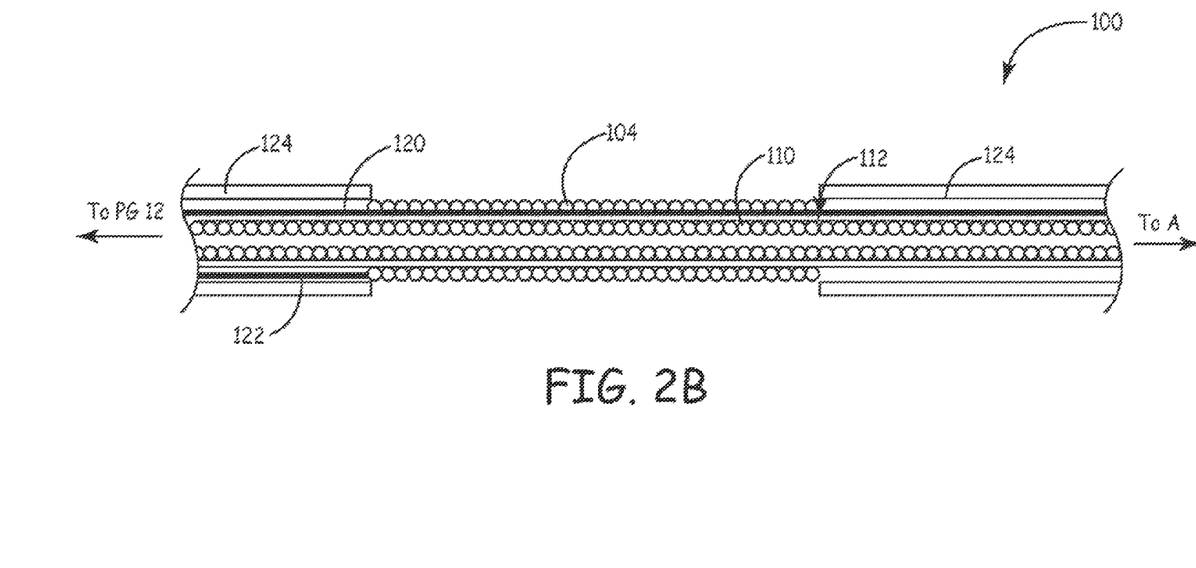
FIG. 2B is a schematic view of a portion of the lead proximal to the distal portion of the lead shown in FIG. 2A.

FIG. 2A is a schematic view of a distal portion of a lead 100 according to an embodiment of the present disclosure. FIG. 2B is a schematic view of a portion of the lead 100 proximal to the distal portion of the lead shown in FIG. 2A. The views of FIGS. 2A and 2B are partially cross-sectional to illustrate the relative positioning of the lead components with respect to each other. The lead 100 is an exemplary configuration for lead 14 in FIG. 1. As is shown, the proximal end of the distal portion of lead 100 shown in FIG. 2A is electrically coupled to the distal end of the proximal portion of lead 100 shown in FIG. 2B.

The lead 100 includes a distal defibrillation coil electrode 102, a proximal defibrillation coil electrode 104, and a tip electrode 108. The distal defibrillation coil electrode 102 and proximal defibrillation coil electrode 104 may be used to deliver a high voltage therapy signal to different portions of the heart 18. The tip electrode 108 may be used for pacing, sensing, or both. In the embodiment shown, the tip electrode 108 includes a passive fixation mechanism 109. In alternative embodiments, the tip electrode 108 comprises a fixation helix or other active fixation mechanism. In some embodiments, the electrode 108 includes platinum or titanium coated with a combination of iridium oxide (IrOx), titanium/nickel (Ti/Ni), black platinum (Pt black), or tantalum oxide (TaO). When shock therapy is not being delivered through the defibrillation coil electrode 102, the defibrillation coil electrode 102 may be used for pacing and/or sensing functions. The lead 100 may be referred to as an integrated bipolar lead. In alternative embodiments, the pacing or sensing electrodes are located elsewhere on the lead 100. The lead 100 may alternatively include fewer or more electrodes.

The tip electrode 108 is coupled to a conductive coil 110, which is surrounded by an insulative layer 112 to insulate the conductive coil 110 from other elements of the lead 100. In some embodiments, the insulative layer 112 extends from the proximal end to the distal end of the lead 100. The insulative layer 112 may be comprised of, for example, silicone material, Teflon, expanded polytetrafluoroethylene (ePTFE), polytetrafluoroethylene (PTFE), ethylene tetrafluoroethylene (ETFE), or another suitable non-conductive material. The electrode 108, the conductive coil 110, and the insulative layer 112 combine to form the low voltage pacing/sensing portion 114 of the lead 100.

The conductive coil 110 extends through the lead 100 and is adapted for connection to the pulse generator 12 at the proximal end of the lead 100. In the embodiment shown, the conductive coil 110 is parallel with the defibrillation coil electrodes 102, 104. The longitudinal axis of the conductive coil 110 is offset from the longitudinal axes of the defibrillation coil electrodes 102, 104. In some embodiments, the conductive coil 110 is coupled to a proximal connector at the proximal end of the lead 100. The connectors at the proximal end of the lead 100 are sized and shaped to interface with a connector block or other component of the pulse generator 12. To reduce the amount of MRI-induced energy that is transmitted to the conductive coil 110, the turns of the conductive coil 110 may be tightly wound to maximize the inductance of the coil. In some embodiments, to minimize the space between adjacent turns and maximize the number of turns, the conductive coil 110 is unifilar. In other embodiments, the conductive coil 110 is multifilar.

The distal defibrillation coil electrode 102 is coupled to a conductive cable 120, and the proximal defibrillation coil electrode 104 is coupled to a conductive cable 122. The conductive cables 120 and 122 extend through the lead 100 and are adapted for connection to the pulse generator 12 at the proximal end of the lead 100. In some embodiments, the conductive cables 120 and 122 may extend through the lead 100 in separate lumens parallel to the conductive coil 110. In some embodiments, the cables 120 and/or 122 are longitudinal wires or filaments of conductive materials. In other embodiments, the cables 120 and/or 122 are small diameter coils. The conductive cables 120, 122 are adjacent an insulating layer 112. In some embodiments, the lead 100 comprises an extruded body including a plurality of lumens to accommodate the conductive coil 110 and conductive cables 120, 122. In such a configuration, the insulating layers adjacent the lead conductors 110, 120, 122 may be integral with each other. In some embodiments, the conductive cables 120 and 122 are each coupled to a proximal connector at the proximal end of the lead 100 that is sized and shaped to interface with a connector block or other component of the pulse generator 12. The conductive cables 120 and 122 deliver a high voltage defibrillation signal from the pulse generator 12 to the defibrillation coil electrodes 102 and 104, respectively. While the conductive cables 120, 122 are shown connected to the proximal ends of the defibrillation coil electrodes 102, 104, respectively, the conductive cables 120, 122 may alternatively be connected to the distal end or both the proximal and distal ends of the defibrillation coil electrodes 102, 104, respectively.

In a magnetic resonance imaging (MRI) environment, the radio frequency (RF) fields can induce a current in the conductive elements of the lead 14. This current may then be dissipated at the point of contact between the lead electrodes and adjacent tissue, resulting in elevated temperatures in the tissue. For example, when the conductive coil 110 and the defibrillation coil electrodes 102, 104 are wound in the same direction, a transformer-like coupling can develop between the conductive coil 110 and the defibrillation coil electrodes 102, 104 at MRI frequencies. Due to this coupling, MRI induced current may be generated in the conductive coil 110 that is dissipated at the electrode 108 in the form of heat.

To reduce the RF current that is transmitted to the electrode 108, the conductive coil 110 is wound in a first direction, and the defibrillation coil electrodes 102, 104 are wound in a second direction opposite the first direction. For example, in some embodiments, the conductive coil 110 is right hand wound and the defibrillation coil electrodes 102, 104 are left hand wound. Alternatively, the conductive coil 110 may be left hand wound and the defibrillation coil electrodes 102, 104 may be right hand wound. By winding the conductive coil 110 in a direction opposite the defibrillation coil electrodes 102, 104, coupling between the conductive coil 110 and the defibrillation coil electrodes 102, 104 is reduced, which reduces heating in the electrode 108.

To further reduce the amount of energy that is transmitted to the defibrillation coil electrodes 102, 104, the turns of the defibrillation coil electrodes 102, 104 may be tightly wound to maximize the inductance of the coil. Also, unifilar coils may be used to minimize the space between adjacent turns and maximize the number of turns in the defibrillation coil electrodes 102, 104. In some embodiments, the filars of the defibrillation coil electrodes 102, 104 have a diameter in the range of about 0.004 to 0.012 inch (about 0.106 mm to 0.305 mm). In alternative embodiments the defibrillation coil electrodes 102, 104 are multifilar and/or the turns of the defibrillation coil electrodes 102, 104 are not tightly wound.

Figure 3:
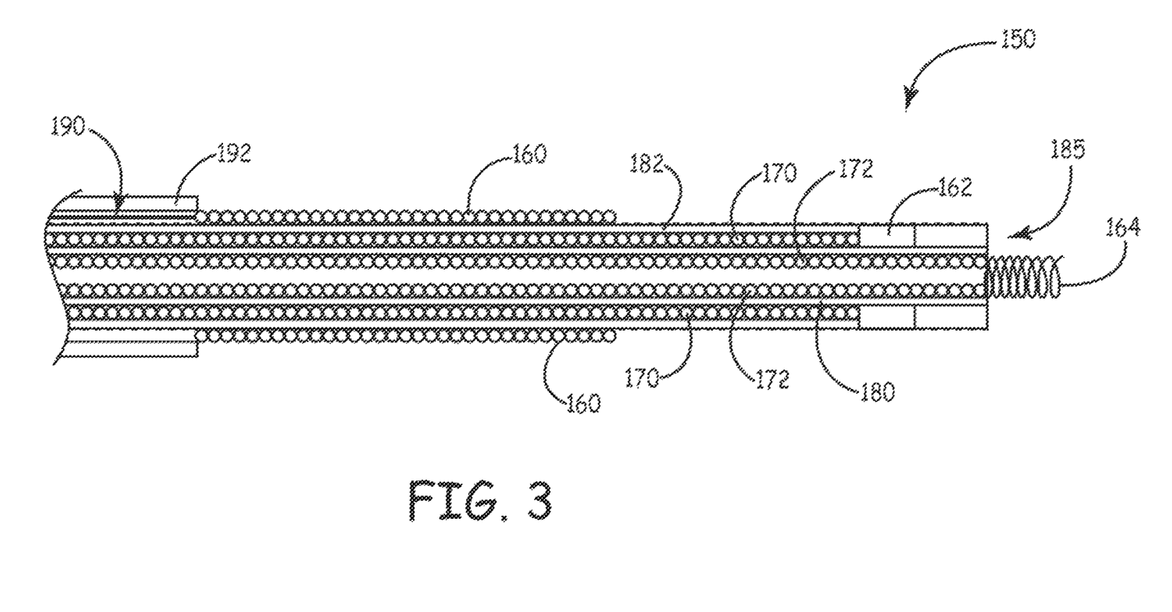
FIG. 3 is a schematic view of a distal portion of a lead according to another embodiment of the present disclosure including a defibrillation coil that is reverse-wound with respect to inner conductive coils.

FIG. 3 is a schematic view of a lead 150 according to another embodiment of the present disclosure. The lead 150 is another exemplary configuration for lead 14 in FIG. 1. The lead 150 includes a defibrillation coil electrode 160, and pacing or sensing electrodes 162 and 164. The defibrillation coil electrode 160 may be used to deliver a high voltage therapy signal to a portion of the heart 18. The pacing or sensing electrodes 162 and 164 may be used for pacing, sensing, or both. In the embodiment shown, the electrode 162 is a ring electrode, and the electrode 164 is a tip electrode including a fixation helix. In an alternative embodiment, the tip electrode 164 is includes a passive fixation mechanism. In some embodiments, the lead 150 only includes a tip electrode 164. The defibrillation coil electrode 160 and the pacing or sensing electrodes 162 and 164 may be located near a distal end portion of the lead 150. In alternative embodiments, the defibrillation and pacing or sensing electrodes are located elsewhere on the lead 150. The lead 150 may also alternatively include fewer or more electrodes.

The electrode 162 is coupled to a first conductive coil 170, and the electrode 164 is coupled to a second conductive coil 172. The second conductive coil 172 is surrounded by an insulative layer 180 to insulate the conductive coil 172 from other elements of the lead 150. In some embodiments, the insulative layer 180 extends from the proximal end to the distal end of the lead 150. An insulative layer 182 is also formed around the first conductive coil 170. In some embodiments, the insulative layer 182 extends from the proximal end of the lead 150 to the electrode 162. With this arrangement, the electrode 162 is exposed at the outer surface of the lead 150 to allow contact with adjacent tissue. The insulative layers 180 and 182 may be comprised of, for example, silicone material, Teflon, expanded polytetrafluoroethylene (ePTFE), polytetrafluoroethylene (PTFE), ethylene tetrafluoroethylene (ETFE), or another suitable non-conductive material. The electrodes 162 and 164, the conductive coils 170 and 172, and the insulative layers 180 and 182 combine to form the low voltage pacing/sensing portion 185 of the lead 150.

The first conductive coil 170 and the second conductive coil 172 extend through the lead 150 and are adapted for connection to the pulse generator 12 at the proximal end of the lead 150. The conductive coils 170, 172 are coaxial with each other. In the embodiment shown, the conductive coils 170, 172 are parallel with the defibrillation coil electrode 160. The longitudinal axes of the conductive coils 170, 172 are offset from the longitudinal axis of the defibrillation coil electrode 160. In some embodiments, the first conductive coil 170 and the second conductive coil 172 are each coupled to a proximal connector at the proximal end of the lead 150. The connectors at the proximal end of the lead 150 are sized and shaped to interface with a connector block or other component of the pulse generator 12. The signals carried by the first conductive coil 170 and the second conductive coil 172 may be independently controlled by the pulse generator 12 such that different signals may be delivered to and/or received from the electrodes 162 and 164. In alternative embodiments, the conductive coils 170, 172 are co-radial.

The inductance of a coil is directly proportional to the square of the number of turns in the coil. To reduce the amount of MRI-induced energy that is transmitted to the conductive coils 170, 172, the turns of the conductive coils 170, 172 may be tightly wound to maximize the inductance of the coil. In some embodiments, to minimize the space between adjacent turns and maximize the number of turns, at least one of the conductive coils 170, 172 is unifilar. In other embodiments, one or both of the conductive coils 170, 172 are multifilar.

The defibrillation coil electrode 160 is coupled to a conductive cable 190, which extends through the lead 150 and is adapted for connection to the pulse generator 12 at the proximal end of the lead 150. The conductive cable 190 may extend through the lead 150 in a lumen parallel to the conductive coils 170 and 172. The conductive cable 190 is surrounded by an insulating layer 192. In some embodiments, the lead 150 comprises an extruded body including a plurality of lumens, one to accommodate the conductive coils 170, 172 and one to accommodate the conductive cable 190. In such a configuration, the insulating layers adjacent the lead conductors 170, 172, and 190 may be integral with each other. In some embodiments, the conductive cable 190 is coupled to a proximal connector at the proximal end of the lead 150 that is sized and shaped to interface with a connector block or other component of the pulse generator 12. The conductive cable 190 delivers a high voltage defibrillation signal from the pulse generator 12 to the defibrillation coil electrode 160. In some uses, the lead 150 is arranged in the heart 18 such that the signal delivered by the defibrillation coil electrode 160 depolarizes a critical mass of the heart muscle, terminates an arrhythmia, and allows normal sinus rhythm to be reestablished. While the conductive cable 190 is shown connected to the proximal end of the defibrillation coil electrode 160, the conductive cable 190 may alternatively be connected to the distal end or both the proximal and distal ends of the defibrillation coil electrode 160.

To reduce the RF current that is transmitted to the electrodes 162, 164, the conductive coils 170, 172 are wound in a first direction, and the defibrillation coil electrode 160 is wound in a second direction opposite the first direction. For example, in some embodiments, the conductive coils 170, 172 are right hand wound and the defibrillation coil electrode 160 is left hand wound. Alternatively, the conductive coils 170, 172 may be left hand wound and the defibrillation coil electrode 160 may be right hand wound. By winding the conductive coils 170, 172 in a direction opposite the defibrillation coil electrode 160, coupling between the conductive coils 170, 172 and the defibrillation coil electrode 160 is reduced, which reduces heating in the electrodes 162, 164.

In order to further reduce the amount of energy that is transmitted to the defibrillation coil electrode 160, the turns of the defibrillation coil electrode 160 may be tightly wound to maximize the inductance of the coil. Also, unifilar coils may be used to minimize the space between adjacent turns and maximize the number of turns in the defibrillation coil electrode 160.

Figure 4:
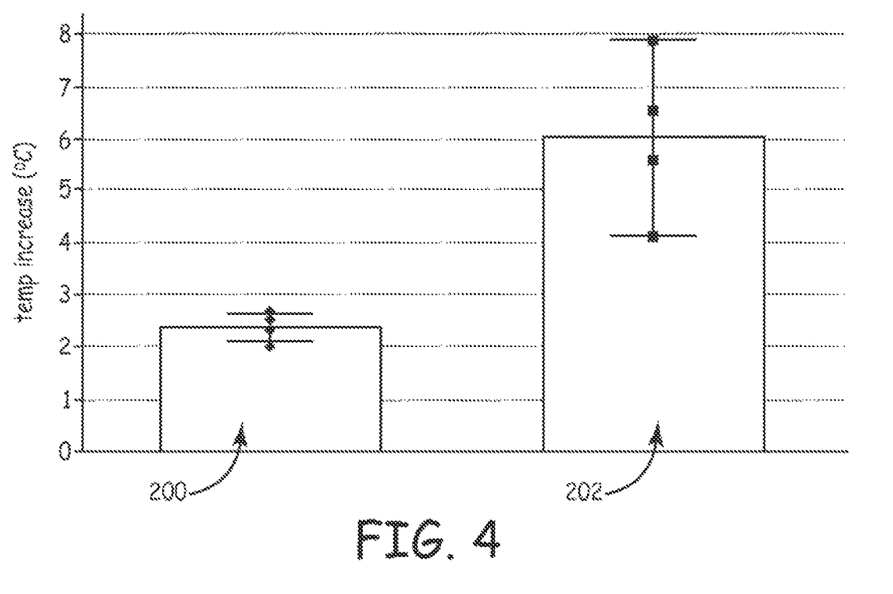
FIG. 4 is a graph comparing measured temperature increase for a lead including an inner conductive coil wound in the opposite direction as the defibrillation coil with a lead including an inner conductive coil wound in the same direction as the defibrillation coil.

FIG. 4 is a graph comparing measured temperature increase for a lead 100 including an inner conductive coil wound in the opposite direction as the defibrillation coil with a lead including an inner conductive coil wound in the same direction as the defibrillation coil. The leads tested were similar to the lead 100 described above with regard to FIGS. 2A and 2B. In the embodiment tested, the inner conductive coil 110 was about 59 centimeters (cm) long and comprised of a unifilar, tightly wound 0.005 inch diameter, MP35N filar with 41 percent silver (Ag) content. The defibrillation coil electrodes 102, 104 each comprised three 0.008 inch platinum clad titanium and platinum filars wound with a 0.027 inch pitch and a 0.079 inch inner diameter.

Bar 200 illustrates the mean temperature increase of the electrode 108 in an MRI environment for a lead 14 having the inner conductive coil 110 wound in the opposite direction as the defibrillation coils 102, 104. Bar 202 illustrates the mean temperature increase of the electrode 108 in an MRI environment for a lead 14 having the inner conductive coil 110 wound in the same direction as the defibrillation coils 102, 104. The plots at the top of each of bars 200, 202 illustrate the range of temperature increases seen in four tests. As is shown, the temperature increase measured at electrode 108 for the defibrillation coils 102, 104 wound in the opposite direction as inner conductive coil 110 was less than 3.0° C., while the temperature increase measured at electrode 108 for coils 102, 104, 110 wound in the same direction was between 4.0° C. and 8.0° C. The median drop in temperature increase between bars 202 and 200 is more than 3.5° C.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A medical device lead comprising:
   a proximal connector configured to couple the lead to a pulse generator;
   an insulative lead body extending distally from the proximal connector;
   an inner conductor coupled to the proximal connector at a proximal end and extending through the lead body;

one or more cable conductors coupled to the proximal connector at a proximal end and extending through the lead body, wherein each of the one or more cable conductors is formed from longitudinal wires or filaments that extend straight along the lead, wherein each of the one or more cable conductors is formed from longitudinal wires or filaments that extend straight along the lead; and one or more defibrillation coil electrodes each coupled to a distal end of one of the one or more cable conductors, the one or more defibrillation coil electrodes each disposed around and electrically isolated from the inner conductor, wherein the one or more defibrillation coil electrodes each have a first winding direction and the inner conductor has a second winding direction opposite the first winding direction.

2. The medical device lead of claim 1, wherein one or more defibrillation coils are separated from the inner conductor by an insulative layer.

3. The medical device lead of claim 1, wherein the inner conductor is coupled to one or more pace/sense electrodes at a distal end of the inner conductor.

4. The medical device lead of claim 1, wherein the inner conductor comprises one or more coils.

5. The medical device lead of claim 4, wherein at least one of the one or more coils is unifilar.

6. A medical device lead comprising:
a first distal electrode;
a first inner conductive coil having a proximal end and a distal end electrically coupled to the first distal electrode;
a cable conductor; and
a defibrillation coil electrode having a proximal end and a distal end, the proximal end of the defibrillation coil electrode coupled to a distal end of the cable conductor, the defibrillation coil parallel with and electrically isolated from the first inner conductive coil, wherein the defibrillation coil is wound in a first winding direction from the proximal end of the defibrillation coil to the distal end of the defibrillation coil, and wherein the first inner conductive coil is wound in a second winding direction opposite the first winding direction from the proximal end of the first inner conductive coil to the distal end of the first inner conductive coil.

7. The medical device lead of claim 6, wherein the defibrillation coil electrode is separated from the first inner conductive coil by an insulative layer.

8. The medical device lead of claim 6, wherein the first inner conductive coil is unifilar.

9. The medical device lead of claim 6, wherein the first distal electrode is a tip electrode.

10. The medical device of claim 6, wherein a temperature increase at the first electrode in an MRI environment is less than about 3.0° C.

11. The medical device lead of claim 6, and further comprising:
a second distal electrode; and
a second inner conductive coil having a distal end electrically coupled to the second distal electrode, wherein the second inner conductive coil has the second winding direction.

12. The medical device lead of claim 11, wherein the second inner conductive coil is unifilar.

13. The medical device lead of claim 11, wherein the second distal electrode is a ring electrode.

14. A medical device comprising:
a pulse generator; and
a lead comprising:
a proximal connector configured to couple the lead to the pulse generator;
an insulative lead body extending distally from the proximal connector, the insulative lead body forming a plurality of lumens;
an inner conductive coil assembly coupled to the proximal connector at a proximal end and extending through the lead body within a first lumen of the plurality of lumens;
one or more cable conductors coupled to the proximal connector at a proximal end and extending through the lead body within a second lumen of the plurality of lumens; and
one or more defibrillation coil electrodes coupled to a distal end of the one or more cable conductors, the one or more defibrillation coil electrodes parallel with and electrically isolated from the inner conductive coil, wherein the one or more defibrillation coil electrodes have a first winding direction and the inner conductive coil has a second winding direction opposite the first winding direction.

15. The medical device of claim 14, wherein the one or more defibrillation coils are separated from the inner conductive coil assembly by an insulative layer.

16. The medical device of claim 14, wherein the inner conductive coil assembly is coupled to one or more pace/sense electrodes at a distal end of the inner conductive coil assembly.

17. The medical device of claim 16, wherein the one or more pace/sense electrodes comprises a tip electrode.

18. The medical device of claim 16, wherein a temperature increase at each of the one or more pace/sense electrodes in an MRI environment is less than about 3.0° C.

19. The medical device of claim 14, wherein the inner conductive coil assembly comprises one or more coils.

20. The medical device of claim 19, wherein at least one of the one or more coils is unifilar.

* * * * *